United States Patent
Yanagawa (10) Patent No.: US 11,841,323 B2
(45) Date of Patent: Dec. 12, 2023

(54) SENSOR SUBSTRATE AND METHOD OF PRODUCING THE SENSOR SUBSTRATE

(71) Applicant: Panasonic Intellectual Property Management Co., Ltd., Osaka (JP)

(72) Inventor: Hiroto Yanagawa, Osaka (JP)

(73) Assignee: Panasonic Intellectual Property Management Co, Ltd., Osaka (JP)

(*) Notice: Subject to any disclaimer, the term of this patent is extended or adjusted under 35 U.S.C. 154(b) by 641 days.

(21) Appl. No.: 17/077,444

(22) Filed: Oct. 22, 2020

(65) Prior Publication Data

US 2021/0041358 A1 Feb. 11, 2021

Related U.S. Application Data

(63) Continuation of application No. PCT/JP2019/025628, filed on Jun. 27, 2019.

(30) Foreign Application Priority Data

Aug. 28, 2018 (JP) ................... 2018-159744

(51) Int. Cl.
  *G01N 21/00* (2006.01)
  *G01N 21/64* (2006.01)
  *G01N 21/65* (2006.01)

(52) U.S. Cl.
  CPC ......... *G01N 21/645* (2013.01); *G01N 21/658* (2013.01); *G01N 2021/6482* (2013.01); *G01N 2201/02* (2013.01)

(58) Field of Classification Search
  CPC .................................................. G01N 21/648
  See application file for complete search history.

(56) References Cited

U.S. PATENT DOCUMENTS

| 2015/0204792 A1 | 7/2015 | Shibayama et al. |
| 2018/0073065 A1* | 3/2018 | Bowen ............... C12Q 1/6844 |
| 2018/0143136 A1 | 5/2018 | Barcelo et al. |

FOREIGN PATENT DOCUMENTS

| JP | 2012-220432 | 11/2012 |
| JP | 2014-048083 | 3/2014 |
| JP | 2015-052562 | 3/2015 |
| JP | 2016-020887 | 2/2016 |
| JP | 2017-503483 | 2/2017 |

(Continued)

OTHER PUBLICATIONS

International Search Report of PCT application No. PCT/JP2019/025628 dated Sep. 10, 2019.

*Primary Examiner* — Dani Fox
(74) *Attorney, Agent, or Firm* — Rimon P.C.; Michael E. Fogarty (57) ABSTRACT

The present disclosure provides a sensor substrate that detects an analyte of a low concentration with high sensitivity and high reliability. The sensor substrate according to the present disclosure a first substrate having first microprotrusions provided on the surface thereof and covered by a metal film, an adhesive film disposed on the surface of the first substrate and having a slit, and a second substrate that is transparent, disposed on the adhesive film, and having a first through hole and a second through hole, wherein each of the first through hole and the second through hole is in communication with the slit, and the first microprotrusions overlap the slit in a plan view.

19 Claims, 11 Drawing Sheets

(56) References Cited

FOREIGN PATENT DOCUMENTS

| JP | 2018-515767 | 6/2018 |
|----|-------------|--------|
| JP | 2018-132339 | 8/2018 |
| WO | 2014/025033 | 2/2014 |
| WO | 2017/027643 | 2/2017 |
| WO | 2017/109057 | 6/2017 |
| WO | 2017/109175 | 6/2017 |

* cited by examiner

SENSOR SUBSTRATE AND METHOD OF PRODUCING THE SENSOR SUBSTRATE

BACKGROUND

1. Technical Field

The present disclosure relates to a sensor substrate that detects an analyte (for example, a virus) in a sample and a method of producing the sensor substrate.

2. Description of the Related Art

A densitometry analyzer using an immunochromatographic method is used for virus detection in hospitals. Japanese Unexamined Patent Application Publication No. 2014-48083 discloses a compact-disc-shaped microchip. In the compact-disc-shaped microchip, a sample solution is centrifugally sent to a detection portion.

SUMMARY

However, the above-described compact-disc-shaped microchip may fail to detect an analyte with high sensitivity and high reliability.

One non-limiting and exemplary embodiment provides a sensor substrate that detects an analyte of low concentration with high sensitivity and high reliability and a method of producing the sensor substrate.

In one general aspect, the techniques disclosed here feature a sensor substrate comprising a first substrate having first microprotrusions provided on the surface thereof and covered by a metal film, an adhesive film disposed on the surface of the first substrate and having a slit, and a second substrate that is transparent, disposed on the adhesive film, and having a first through hole and a second through hole, wherein each of the first through hole and the second through hole is in communication with the slit, and the first microprotrusions overlap the slit in a plan view.

According to the present disclosure, an analyte of low concentration is detected with high sensitivity and high reliability.

It should be noted that general or specific embodiments may be implemented as a system, a method, an integrated circuit, a computer program, a computer readable storage medium such as a CD-ROM, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Underlying Knowledge Forming Basis of the Present Disclosure

The above-described known technology may fail to detect an analyte with high sensitivity and high reliability. The inventor of the present disclosure found the reason for the failure. The reason is described below.

Figure 1:
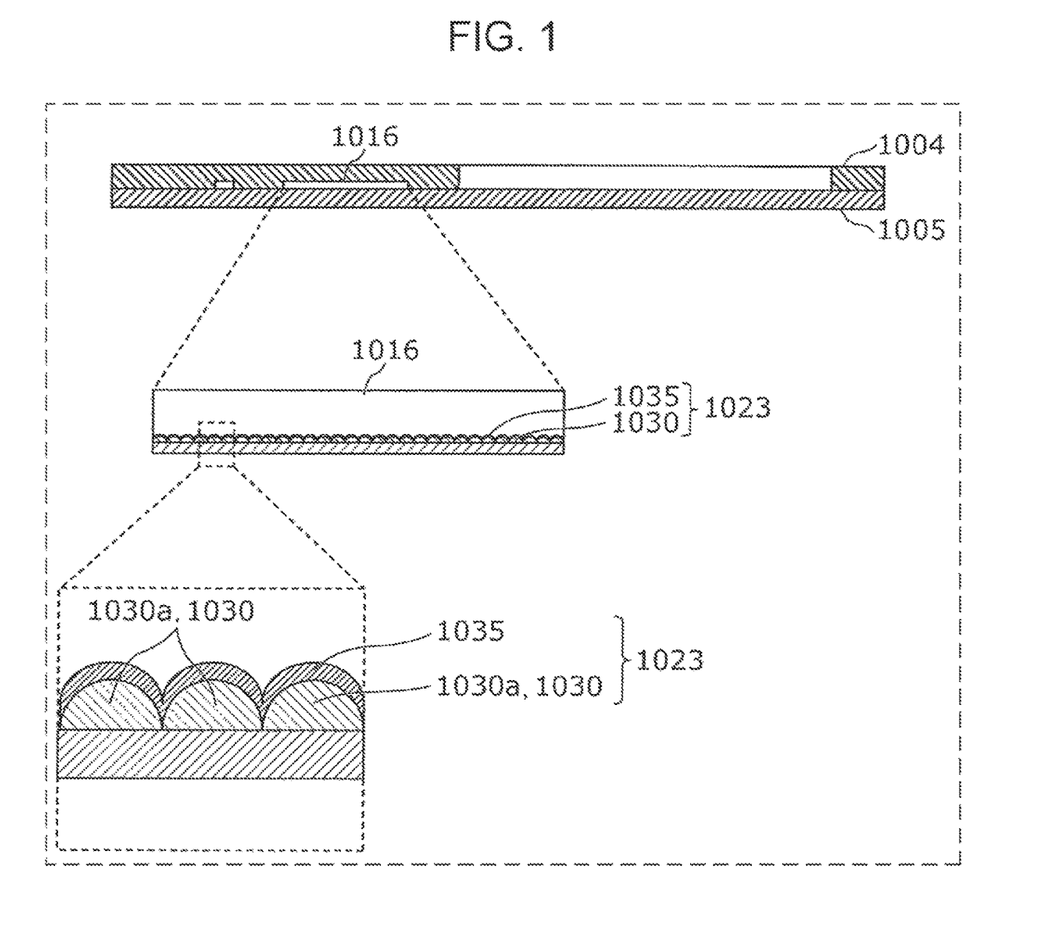
FIG. 1 is a sectional view illustrating a compact-disc-shaped microchip disclosed in Japanese Unexamined Patent Application Publication No. 2014-48083.

FIG. 1 is a sectional view illustrating a compact-disc-shaped microchip disclosed in Japanese Unexamined Patent Application Publication No. 2014-48083. In Japanese Unexamined Patent Application Publication No. 2014-48083, the compact-disc-shaped microchip includes an upper first disc 1004 and a lower second disc 1005. A detection portion 1016 is located between the first disc 1004 and the second disc 1005. The detection portion 1016 is constituted by a light-transmitting recess in the first disc 1004 and a transmission surface plasmon resonance sensor 1023 on the second disc 1005. The transmission surface plasmon resonance sensor 1023 includes a beaded layer 1030 including spherical beads 1030a arranged in a plane and a metal layer 1035 covering the beaded layer 1030.

As described above, the first disc 1004 has a recess. The formation of the recess may damage the first disc 1004, and the damage may lower the light-transmitting properties of the recess, for example, making it difficult to provide the recess with the light-transmitting properties high enough for photodetection.

Furthermore, the first disc 1004 and the second disc 1005 are attached to each other with an adhesive. The adhesive is likely to flow into the transmission surface plasmon resonance sensor 1023 during manufacturing. The amount of adhesive may be reduced to prevent the adhesive from flowing into the transmission surface plasmon resonance sensor 1023. However, this lowers the adhesion between the first disc 1004 and the second disc 1005.

Furthermore, the use of the adhesive requires a curing process to cure the adhesive. In the curing process, energy in the form of UV or heat, for example, is applied to the sensor substrate. This may denature the biomaterial immobilized on the substrate.

A sensor substrate developed to solve the problems is described in detail by using an embodiment and with reference to the drawings.

The embodiment described below provides a general or specific example. The numerical values, shapes, materials, components, arrangement and connection of the components, steps, order of the steps, and others described in the following embodiment are mere examples and do not limit the present disclosure. Furthermore, among the components in the following embodiment, the components not recited in the independent claims, which represent superordinate concepts, are described as optional components.

The drawings do not precisely illustrate the components. In the drawings, the substantially identical components are assigned the same reference symbols and the explanation thereof is omitted or simplified.

In the following embodiment, the analyte is a component of a virus floating in the air (hereinafter, simply referred to as a virus). However, the analyte in this disclosure is not limited to the virus. Examples of the component of the virus include a protein and a nucleic acid in the virus. The kind of the virus is not particularly limited and may be any kind generally classified as a virus. The analyte may be anything other than the virus.

Embodiment 1

Outline of Detection System

Figure 2:
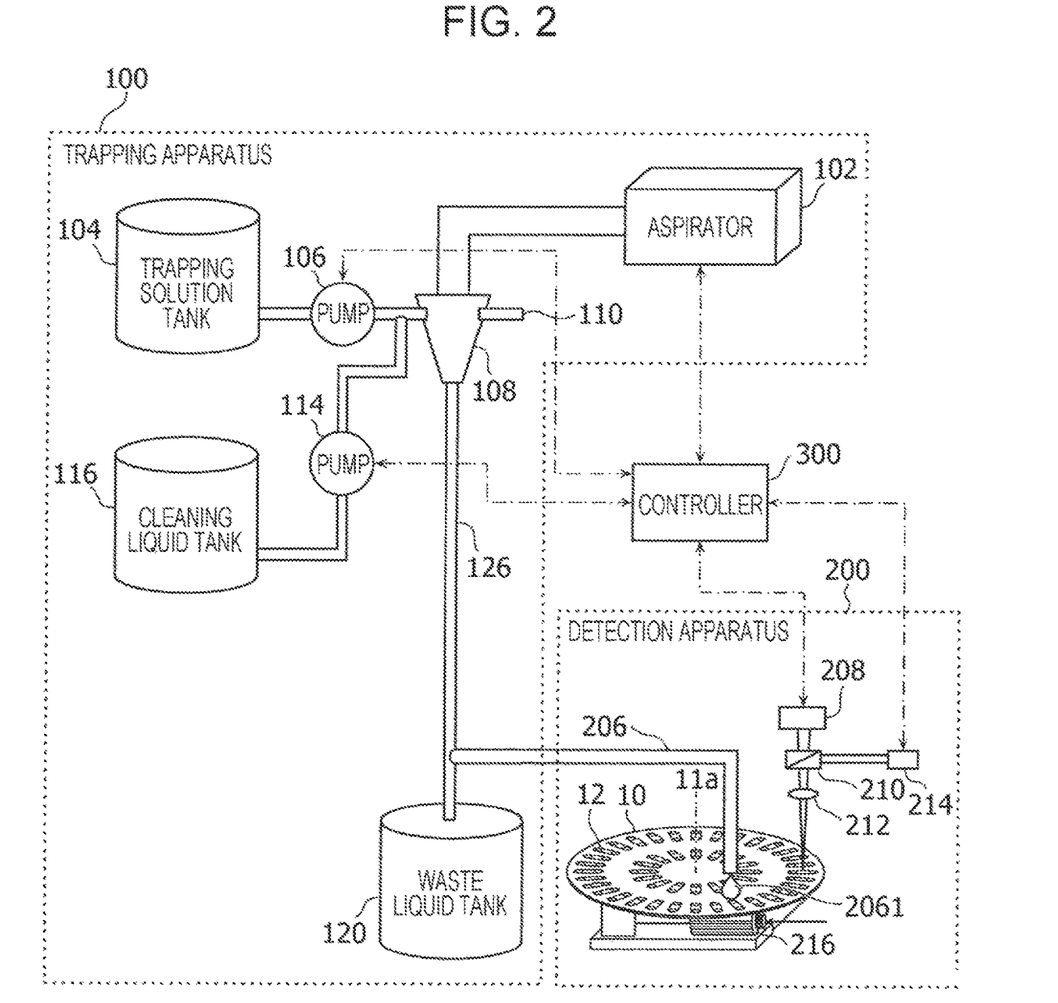
FIG. 2 is a schematic view illustrating a detection system according to Embodiment 1.

FIG. 2 is a schematic view illustrating a detection system according to Embodiment 1. The detection system is installed in a high-traffic room, for example. As illustrated in FIG. 2, the detection system includes a trapping apparatus 100, a detection apparatus 200, and a controller 300. Hereinafter, the trapping apparatus 100, the detection apparatus 200, and the controller 300 are described in detail.

Configuration of Trapping Apparatus

The trapping apparatus 100 traps microparticles in the air, which possibly contain a virus, and mixes the microparticles with a trapping solution. As illustrated in FIG. 2, the trapping apparatus 100 includes an aspirator 102, a trapping solution tank 104, a pump 106, a cyclone 108, an air inlet 110, a cleaning liquid tank 116, a pump 114, a waste liquid tank 120, and a liquid passage 126. Hereinafter, the components of the trapping apparatus 100 are described.

The aspirator 102 collects the ambient air by suction through the air inlet 110. The microparticles possibly containing a virus floating in the ambient air are collected together with the air into the cyclone 108 through the air inlet 110 by suction.

The trapping solution tank 104 is a container holding the trapping solution for trapping a virus in the air.

The pump 106 supplies the trapping solution in the trapping solution tank 104 to the cyclone 108.

The cyclone 108 is connected to the air inlet 110 and the trapping solution tank 104. The cyclone 108 mixes the microparticles in the air, which have been collected by the aspirator 102 through the air inlet 110 by suction and possibly contain a virus, with the trapping solution supplied from the trapping solution tank 104 by the pump 106. The cyclone 108 is connected to the detection apparatus 200 through the liquid passage 126. The trapping solution mixed with the microparticles (hereinafter, referred to as a sample) in the cyclone 108 is discharged to the detection apparatus 200 through the liquid passage 126.

The cleaning liquid tank 116 is a container holding a cleaning liquid for cleaning the cyclone 108 and the liquid passage 126. The cleaning liquid tank 116 is connected to the cyclone 108, and the cleaning liquid in the cleaning liquid tank 116 is supplied to the cyclone 108 by the pump 114.

The waste liquid tank 120 is a container for storing a waste liquid. The waste liquid tank 120 stores, for example, a cleaning liquid that was used to clean the cyclone 108.

The liquid passage 126 is a route that guides the sample discharged from the cyclone 108 to the detection apparatus 200.

Configuration of Detection Apparatus

Next, the detection apparatus 200 is described.

The detection apparatus 200 detects a virus in the trapping solution that has been mixed with the microparticles by the trapping apparatus 100. As illustrated in FIG. 2, the detection apparatus 200 includes a sensor substrate 10, an introduction portion 206, a light source 208, a beam splitter 210, a lens 212, a detection portion 214, and a rotary member 216. Hereinafter, the components of the detection apparatus 200 are described in detail.

The sensor substrate 10 is rotatable about a rotation axis 11a, which is a straight line perpendicular to the main surface. The sensor substrate 10 has measuring portions 12 on the same main surface. In this embodiment, the sensor substrate 10 has a rotationally symmetrically shape about the rotation axis 11a. Specifically described, the sensor substrate 10 has a disc-like shape. The measuring portions 12 each include a metal microstructure in which an immobilized antibody is immobilized. The sensor substrate 10 is described in detail later with reference to FIGS. 2 and 3.

The introduction portion 206 introduces a labelled antibody and a sample to the measuring portions 12. Specifically described, the introduction portion 206 drops a sample 206l including a labelled antibody and the sample onto the measuring portions 12. The labelled antibody is an antibody labelled with a fluorescent substance. The sample is a liquid possibly containing a virus. In this embodiment, the sample is a trapping solution discharged from the cyclone 108.

When the sample contains a virus, the virus is bound to the metal microstructure via an immobilized antibody. At this time, the virus is also bound to the labelled antibody labelled with a fluorescent substance. In other words, a composite of the immobilized antibody, the virus, the labelled antibody, and the fluorescent substance is bound to the metal microstructure. When the metal microstructure in this state is irradiated with light, the fluorescent substance indirectly bound to the virus produces fluorescence and the fluorescence is enhanced by surface plasmons. Hereinafter, the fluorescence enhanced by surface plasmons is referred to as surface-enhanced fluorescence.

The light source 208 is an example of a light emitter that applies excitation light to the measuring portions 12. The light source 208 may employ any known technology without limitation. For example, a laser such as a semiconductor laser and a gas laser may be used as the light source 208. The light source 208 applies excitation light preferably having a wavelength in a range of, for example, 400 nm to 2000 nm, which allows less interaction with a substance contained in the virus. Furthermore, the wavelength of the excitation light is preferably in a range of 600 nm to 850 nm, which is covered by a semiconductor laser.

The beam splitter 210 separates the surface-enhanced fluorescence produced at the measuring portion 12 from the excitation light emitted from the light source 208. Specifically described, the beam splitter 210 transmits the excitation light from the light source 208, separates the surface-enhanced fluorescence produced at the measuring portions 12, and guides it to the detection portion 214.

The lens 212 focuses the excitation light emitted by the light source 208 and passed through the beam splitter 210 onto a detection area 204b.

The detection portion 214 separates the surface-enhanced fluorescence guided by the beam splitter 210 and detects the light in a specific wavelength range to output an electric signal corresponding to the virus level in the sample. The detection portion 214 may employ any known technology that can detect light in a specific wavelength range without limitation. Examples of the detection portion 214 include an interference filter that transmits light in a specific wavelength range to separate light, a Czerny-Turner spectrometer using a grating to separate the light, and an echelle spectrometer. Furthermore, the detection portion 214 may include a notch filter that removes the excitation light emitted by the light source 208 or a longpass filter that blocks the excitation light emitted by the light source 208 and transmits the surface-enhanced fluorescence produced at the measuring portion 12.

Configuration of Controller

The controller 300 controls the operations of the overall detection system. Specifically described, the controller 300 controls the trapping apparatus 100 and the detection apparatus 200.

More specifically described, the controller 300 controls the start of the measurement. The controller 300 causes the aspirator 102 to start collecting the ambient air by suction and causes the pump 106 to supply the trapping solution in the trapping solution tank 104 to the cyclone 108. Thus, the trapping solution and the microparticles are mixed in the cyclone 108, and the sample is supplied from the cyclone 108 to the detection apparatus 200. Furthermore, the controller 300 causes the light source 208 to emit light and causes the detection portion 214 to detect the surface-enhanced fluorescence.

For example, the controller 300 is capable of controlling the pumps to supply the sample of a predetermined volume to the detection apparatus 200 based on the input parameter under the predetermined conditions. Furthermore, the controller 300 has a clock function and may generate and record information about times required for operations. Furthermore, the controller 300 may receive the measured values from the detection apparatus 200 and calculate the change in concentration of the virus floating in the air with passage of time based on the measured values and the time information.

The controller 300 is composed of at least one dedicated electric circuit, for example. The at least one dedicated electric circuit may be disposed on one chip or multiple different chips. Alternatively, the controller 300 may be composed of a general-purpose processer (not illustrated) and a memory (not illustrated) storing software programs or instructions, instead of at least one dedicated electric circuit. In such a case, the processor functions as the controller 300 when the software program or the instruction is executed.

Configuration of Sensor Substrate

Figure 3:
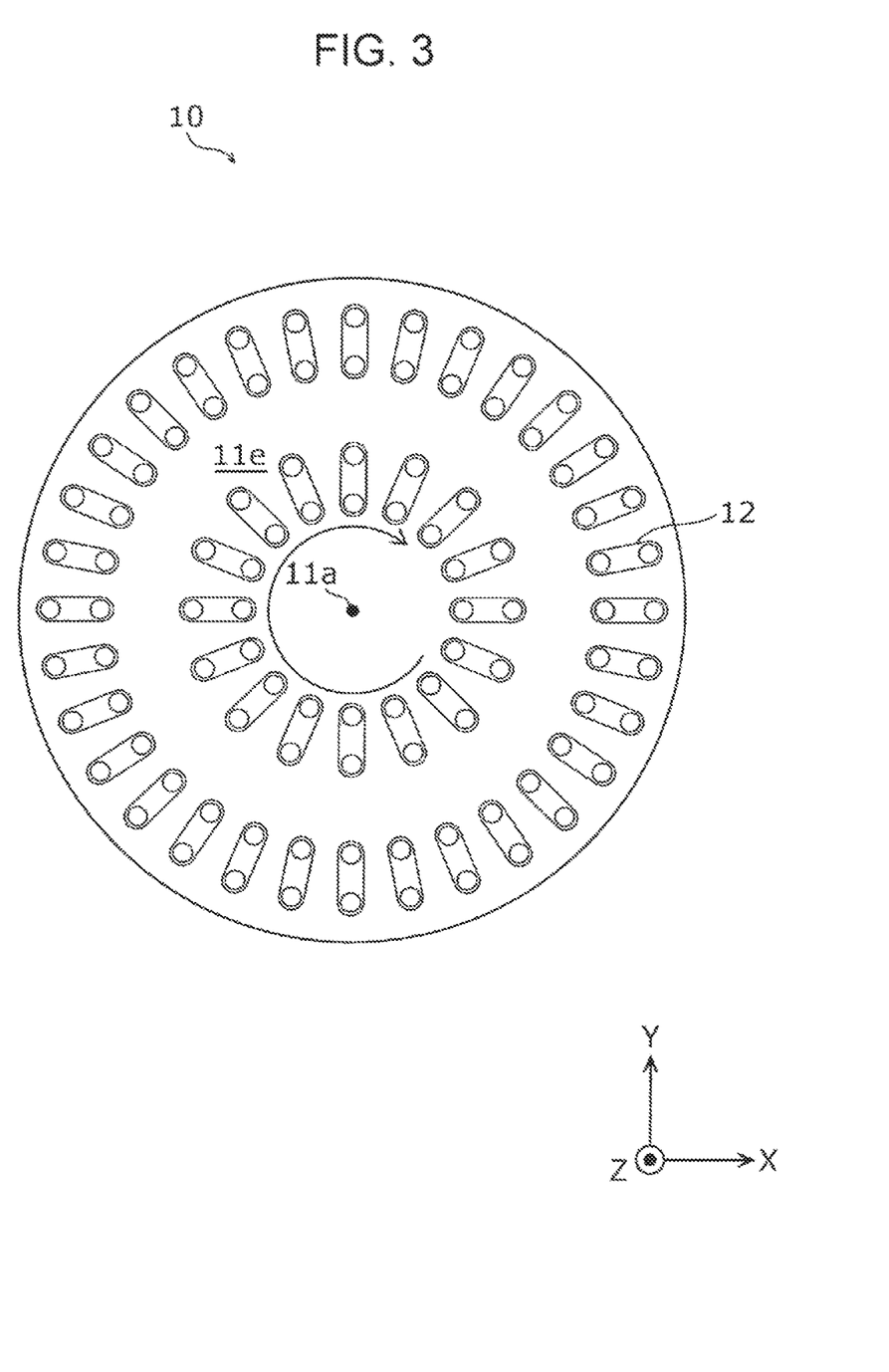
FIG. 3 is a plan view illustrating a sensor substrate according to an embodiment.
Figure 4:
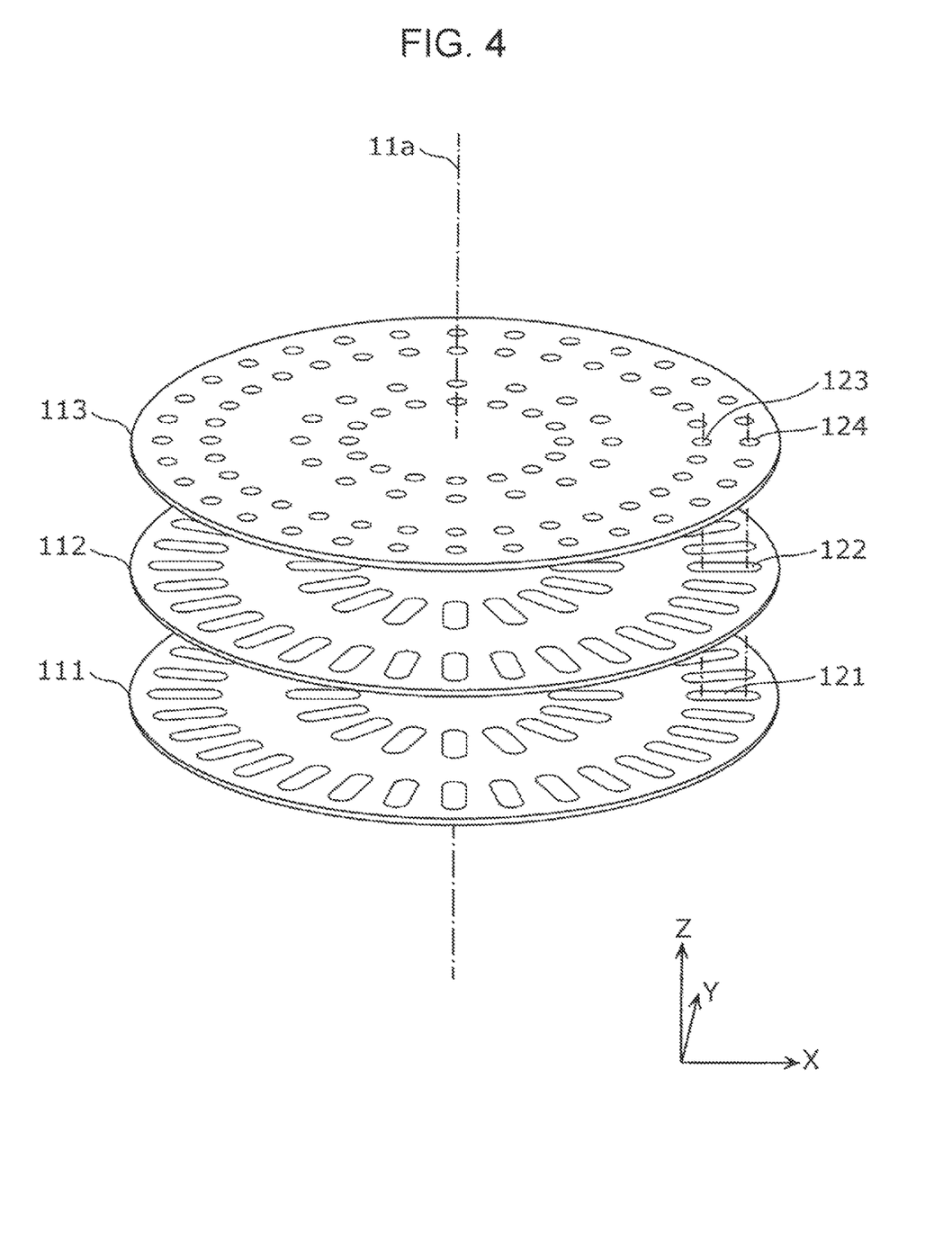
FIG. 4 is an exploded perspective view illustrating the sensor substrate according to the embodiment.

The configuration of the sensor substrate 10 is described in detail with reference to FIGS. 3 and 4. FIG. 3 is a plan view illustrating the sensor substrate 10 according to the present embodiment. FIG. 4 is an exploded perspective view illustrating the sensor substrate 10 according to the present embodiment.

As illustrated in FIG. 3, the sensor substrate 10 is arranged rotatably about the rotation axis 11a, which is a straight line perpendicular to a main surface 11e of the sensor substrate 10 passing through the center of the sensor substrate 10. The measuring portions 12 are arranged on the main surface 11e of the sensor substrate 10 in the circumferential direction of the sensor substrate 10. Specifically described, 16 measuring portions 12 are located on the radially inner side of the sensor substrate 10 and 32 measuring portions 12 are located on the radially outer side of the sensor substrate 10.

Furthermore, as illustrated in FIG. 4, the sensor substrate 10 includes a first substrate 111, an adhesive film 112, and a second substrate 113.

The first substrate 111 is a resin substrate such as an olefin substrate. The first substrate 111 has microprotrusions on the surface. The microprotrusions are partly covered by a metal film to form metal microstructures 121. Hereinafter, the microprotrusions covered by the metal film are referred to as first microprotrusions. The microprotrusions around the first microprotrusions are referred to as second microprotrusions. The metal microstructures 121 are spaced apart from each other in the circumferential direction of the sensor substrate 10.

The adhesive film 112 is a two-sided adhesive film on the first substrate 111. The adhesive film 112 has slits 122 spaced apart from each other in the circumferential direction of the sensor substrate 10. The slits 122 form flow passages spaced apart from each other. The slits 122 are through holes each having an oval shape elongated in the radial direction of the sensor substrate 10. The slits 122 are arranged at positions corresponding one-to-one with the metal microstructures 121 on the first substrate 111. Thus, the metal microstructures 121 each overlap corresponding one of the slits in plan view. In other words, the metal microstructures 121 correspond one-to-one with the slits 122.

The adhesive film 112 may contain a silicone adhesive. This reduces leakage of residual monomers to the metal microstructure 121. Furthermore, the adhesive film 112 may have a three-layer structure including, in this order, a silicone adhesive layer, a polyimide layer, and a silicone adhesive layer. This improves the strength of the adhesive film 112 and reduces deformation of the sensor substrate 10. The adhesive film 112 may have a single-layer structure including a silicone adhesive layer. Furthermore, the material of the adhesive film is not limited to a silicone adhesive and polyimide.

The second substrate 113 is, for example, a transparent sheet formed of glass or resin and is disposed on the adhesive film 112. Specifically described, the second substrate 113 may be a polycarbonate substrate. The polycarbonate substrate is a versatile material widely used as a material of an optical disc such as a DVD and is a low-cost and readily-processable material. The second substrate 113 has sets of a supply hole 123 and a discharge hole 124 arranged in the radial direction of the sensor substrate 10, and the sets are spaced apart from each other in the circumferential direction of the sensor substrate 10. The supply holes 123 and the discharge holes 124 are circular holes extending through the cover sheet. The supply hole 123 is located inwardly of the discharge hole 124 (closer to the rotation axis 11a) in each set.

The second substrate 113 does not need to have a recess that forms a flow passage. Thus, the light transmitting properties of the second substrate 113 is not lowered by the recess.

The sets of the supply hole 123 and the discharge hole 124 are arranged at positions corresponding one-to-one with the slits 122. In this configuration, the sets of the supply hole 123 and the discharge hole 124 are positioned in the corresponding flow passages. In other words, the sets of the supply hole 123 and the discharge hole 124 are each in communication with corresponding one of the slits.

The measuring portions 12 are each composed of one of the metal microstructures 121, one of the slits 122, and one of the sets of the supply hole 123 and the discharge hole 124.

Configuration of Measuring Portion

Figure 5:
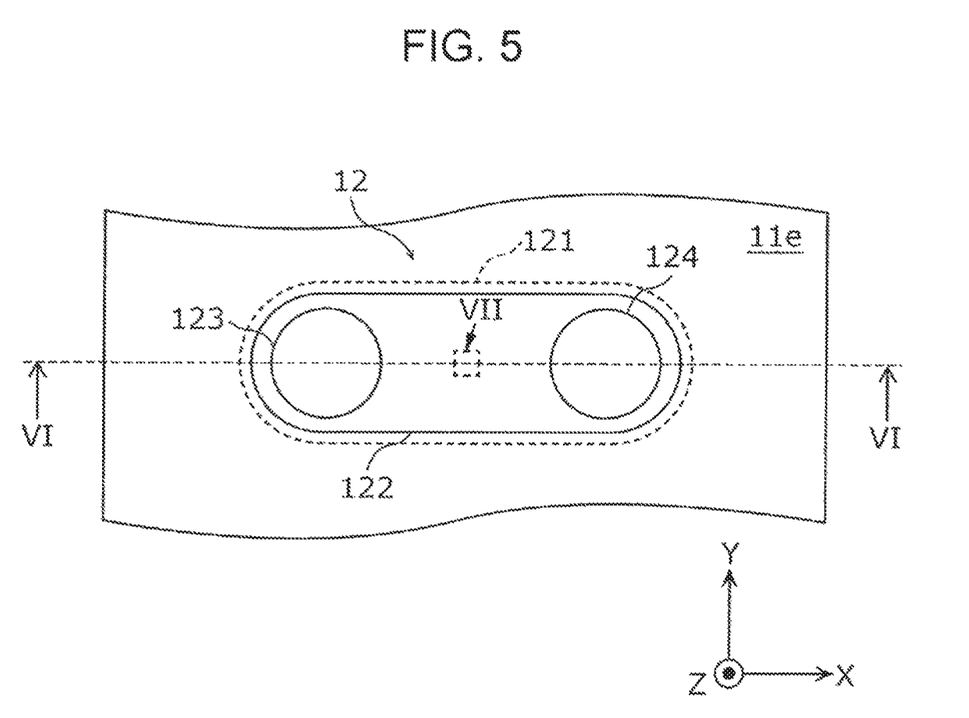
FIG. 5 is a plan view illustrating a measuring portion of the sensor substrate according to the embodiment.
Figure 6:
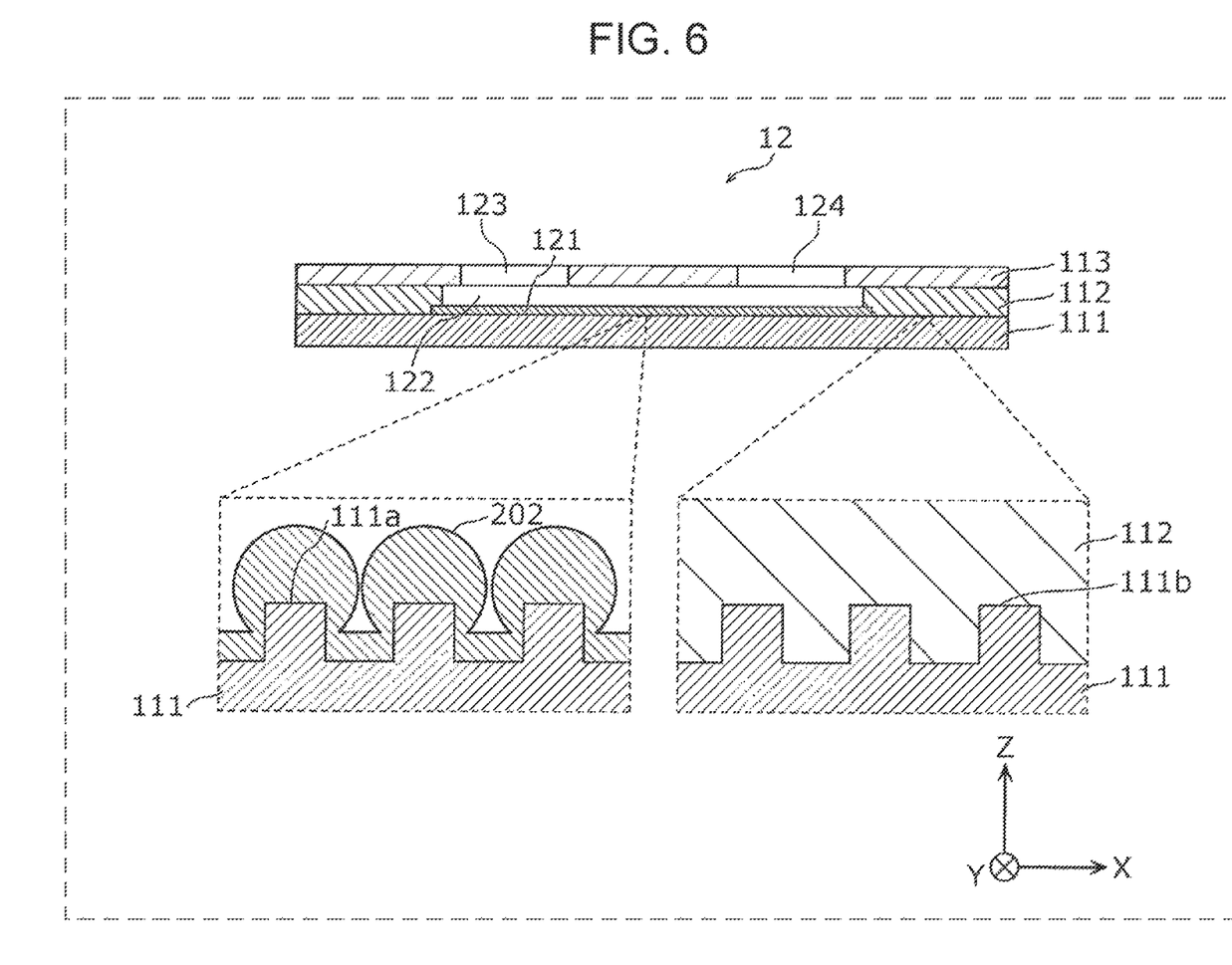
FIG. 6 is a sectional view illustrating the measuring portion of the sensor substrate according to the embodiment.

Herein, the configuration of the measuring portion is described with reference to FIGS. 5 and 6. FIG. 5 is a plan view illustrating the measuring portion 12 of the sensor substrate 10 according to the present embodiment. FIG. 6 is a sectional view illustrating the measuring portion 12 of the sensor substrate 10 according to the present embodiment. Specifically described, FIG. 6 is a sectional view taken along line VI-VI in FIG. 5.

Although one of the measuring portions 12 is described here, the other measuring portions 12 have substantially the same configuration unless otherwise described.

As illustrated in FIGS. 5 and 6, the measuring portion 12 includes the metal microstructure 121, the slit 122, the supply hole 123, and the discharge hole 124.

The introduction portion 206 drops the sample 2061 containing a labelled antibody and a virus into the supply hole 123. The sample 2061 passed through the supply hole 123 moves in the slit 122 along a surface of the metal microstructure 121 in a radially outward direction (toward a peripheral edge of the sensor substrate 10) to the discharge hole 124 due to a centrifugal force produced by the rotation of the sensor substrate 10. At this time, the composite of the labelled antibody and the virus contained in the sample 2061 is bound to the immobilized antibody immobilized on the metal microstructure 121.

After the sample 2061 in the slit 122 is discharged through the discharge hole 124, the metal microstructure 121 is cleaned. Thus, the excess labelled antibody that was not bound to the virus is removed from the metal microstructure 121. The labelled antibody bound to the immobilized antibody remains in the metal microstructure 121.

Configuration of Metal Microstructure

Figure 7:
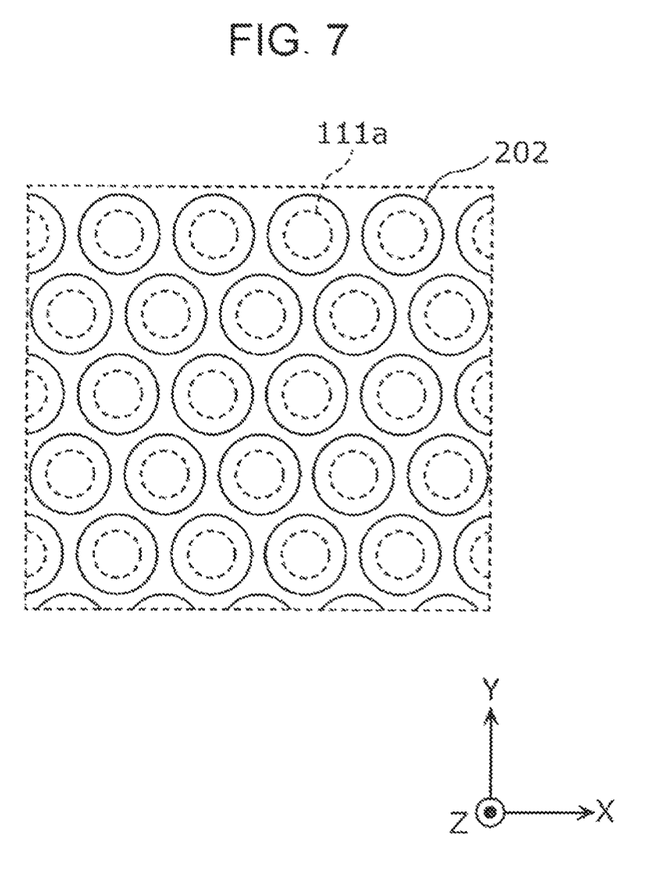
FIG. 7 is a plan view illustrating a portion of a metal microstructure in the embodiment.

Next, the configuration of the metal microstructure 121 is described with reference to FIGS. 6 and 7. FIG. 7 is a plan view illustrating a portion of the metal microstructure 121 in the present embodiment. Specifically described, FIG. 7 is a magnified view of an area VII in FIG. 5.

As illustrated in FIG. 6, the measuring portion 12 includes the nanoscale metal microstructure 121, which produces surface plasmons. The metal microstructure 121 is a portion of the first substrate 111 covered by a metal film 202.

The first substrate 111 has a nanostructure formed by using a nanoimprint technology or an injection molding technology over an entire main surface. The nanostructure includes first microprotrusions 111a and second microprotrusions 111b disposed around the first microprotrusions 111a. The first substrate 111 does not need to have the microprotrusions over the entire surface. For example, the second microprotrusions 111b may be formed only around the first microprotrusions 111a.

The first substrate 111 has the first microprotrusions 111a in sections covered by the metal film 202. As illustrated in FIG. 7, the first microprotrusions 111a are arranged at a regular interval. In this embodiment, the first microprotrusions 111a are arranged in an equilateral triangular lattice. The equilateral triangular lattice may be called a hexagonal lattice or p6m. The arrangement of the first microprotrusions 111a is not limited to the equilateral triangular lattice and may be a square lattice.

The first substrate 111 has the second microprotrusions 111b in sections not covered by the metal film 202 and the second microprotrusions 111b surround the first microprotrusions 111a. The second microprotrusions 111b are arranged at a regular interval as the first microprotrusions 111a. In this embodiment, the second microprotrusions 111b are arranged in an equilateral triangular lattice. The arrangement of the second microprotrusions 111b is not limited to the equilateral triangular lattice and may be a square lattice.

The first microprotrusions 111a and the second microprotrusions 111b each have a cylindrical shape. In the first microprotrusions 111a and the second microprotrusions 111b, the proportion of the height to the pitch is preferably in a range of 1:1 to 1:3. In this embodiment, the wavelength of the excitation light and the wavelength of the fluorescent light are in a range of 750 nm to 850 nm. Thus, in this embodiment, the height of the first microprotrusions 111a and the second microprotrusions 111b is preferably greater than or equal to about 100 nm and less than or equal to about 300 nm and the diameter thereof is preferably greater than or equal to about 150 nm and less than or equal to about 250 nm, and the pitch is preferably greater than or equal to about 300 nm and less than or equal to about 500 nm. When this condition is satisfied, surface plasmons having a resonant wavelength in a wavelength range of 750 nm to 850 nm are generated. The shape of the nanostructure of the first substrate 111 is not limited to this. The microprotrusions may have a semi-spherical shape instead of the cylindrical shape.

The metal film 202 is obtained by forming a metal film on the first substrate 111. When the wavelength of the excitation light and the wavelength of the fluorescent light are in a range of 750 nm to 850 nm, the thickness of the metal film 202 is preferably about 400 nm. Furthermore, the gap dimension between the adjacent metal protrusions of the first microprotrusions 111a covered by the metal film 202 is preferably 100% to 200% of the total of the length of the immobilized antibody, the length of the analyte, and the length of the labelled antibody.

The material of the metal film 202 is not limited to a particular material. The material may be gold, silver, copper, aluminum, or an alloy containing any one of the metals as a main component. In this embodiment, the metal film 202 is formed by sputtering. However, the method of forming the metal film 202 is not limited to the sputtering and the metal film 202 may be formed by an electron beam (EB) deposition method or a vacuum deposition method.

Configuration of Linker Material

Figure 8:
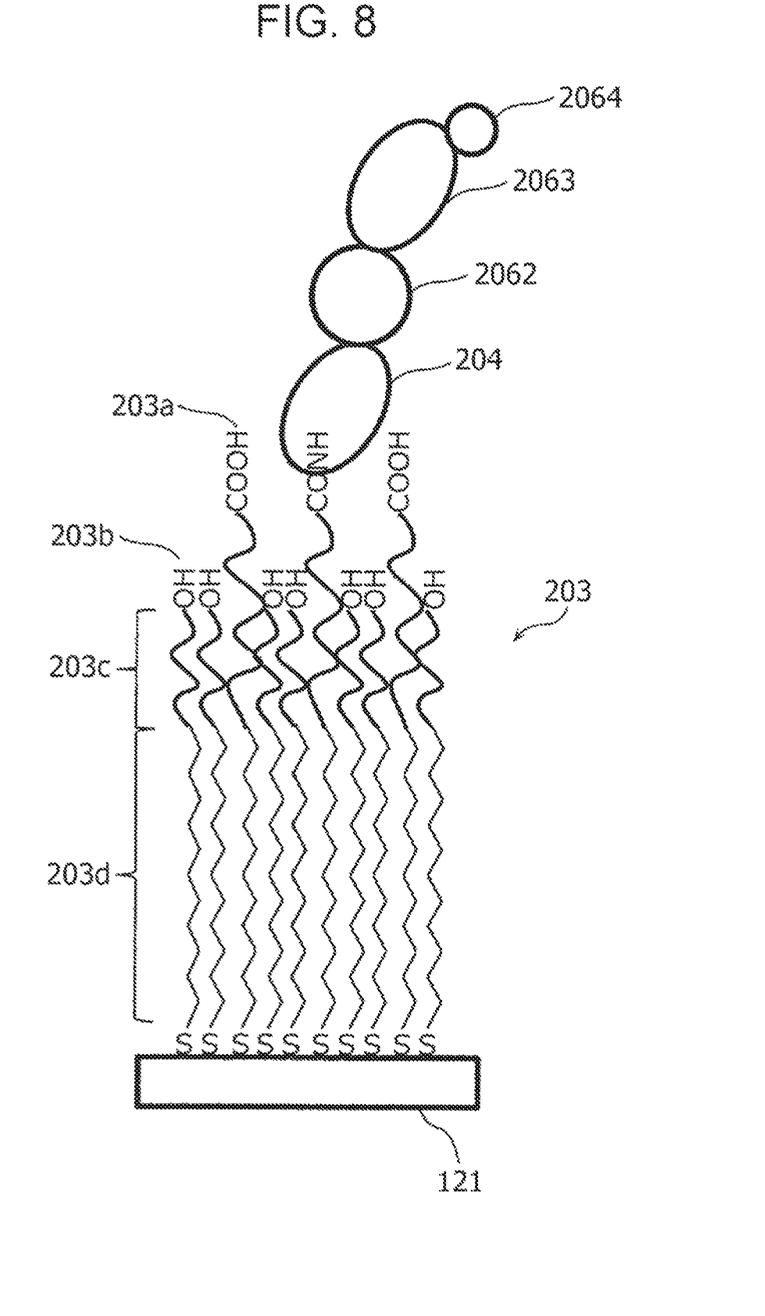
FIG. 8 is a view for explaining a linker material in the embodiment.

Here, the linker material that immobilizes the immobilized antibody on the metal microstructure 121 is described in detail with reference to FIG. 8. FIG. 8 is an explanatory view illustrating a linker material 203 in the present embodiment.

As illustrated in FIG. 8, the metal microstructure 121 is covered by the linker material 203. The linker material 203 here is a self-assembled monolayer (hereinafter, referred to as a SAM film) including linker molecules 203a and non-linker molecules 203b. An immobilized antibody 204 is immobilized on the metal microstructure 121 through the linker molecules 203a.

The linker molecule 203a has a thiol group at one end and a carboxyl group at the other end. The thiol group is bound to the surface of the metal microstructure 121. The carboxyl group forms a peptide bond with the immobilized antibody 204.

Furthermore, the linker molecule 203a has an alkyl chain 203d with greater than or equal to 10 carbon atoms and a polyethylene glycol chain 203c between the thiol group and the carboxyl group. Specifically described, the alkyl chain 203d is connected to the thiol group and the polyethylene glycol chain 203c, and the polyethylene glycol chain 203c is connected to the alkyl chain 203d and the carboxyl group.

The non-linker molecule 203b has a thiol group at one end and a hydroxyl group at the other end. The thiol group is bound to the surface of the metal microstructure 121. The hydroxyl group, which is hydrophilic, reduces nonspecific adsorption of a labelled antibody 2063 and a fluorescent substance 2064.

Furthermore, the non-linker molecule 203b has the alkyl chain 203d with greater than or equal to 10 carbon atoms and the polyethylene glycol chain 203c between the thiol group and the hydroxyl group. Specifically described, the alkyl chain 203d is connected to the thiol group and the polyethylene glycol chain 203c, and the polyethylene glycol chain 203c is connected to the alkyl chain 203d and the hydroxyl group.

In this embodiment, the linker molecules 203a are fewer than the non-linker molecules 203b in the linker material 203.

When the sample 2061 contains a virus (analyte) 2062, the virus 2062 is bound to the immobilized antibody 204 immobilized on the metal microstructure 121. The labelled antibody 2063 labelled with the fluorescent substance 2064 is also bound to the virus 2062.

When the above metal microstructure 121 is irradiated with the excitation light, the fluorescent substance 2064 produces fluorescence and the fluorescence is enhanced by the surface plasmon generated at the metal microstructure 121. In other words, the surface-enhanced fluorescence has an intensity corresponding to the amount of virus.

The immobilized antibody 204 is an example of a first specific binding substance bound specifically to the analyte and may be a VHH antibody. The labelled antibody 2063 is an example of a second specific binding substance bound specifically to the analyte and may be a VHH antibody. The immobilized antibody 204 and the labelled antibody 2063 are not limited to a VHH antibody and may be an IgG antibody.

Operation of Detection Apparatus

Figure 9:
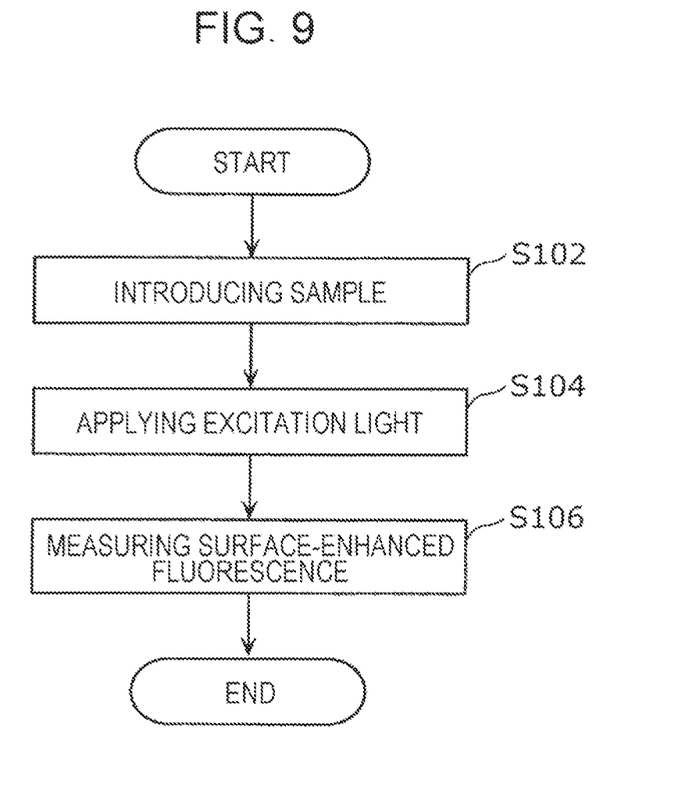
FIG. 9 is a flow chart indicating a virus detection method using the sensor substrate according to the embodiment.

The operation of the detection apparatus 200 having the above-described configuration is described with reference to FIG. 9. FIG. 9 is a flow chart indicating how a virus is detected by using the sensor substrate 10 according to the present embodiment.

First, the introduction portion 206 introduces the sample 2061 possibly containing a virus to the measuring portion 12 (S102). Next, the light source 208 applies excitation light to the metal microstructure 121 of the measuring portion 12 having the sample 2061 (S104). The detection portion 214 measures the fluorescence, which was produced by the fluorescent substance 2064 when irradiated with the excitation light and was enhanced by the surface plasmon, to detect the virus in the sample 2061 (S106).

Method of Producing Sensor Substrate

Figure 10:
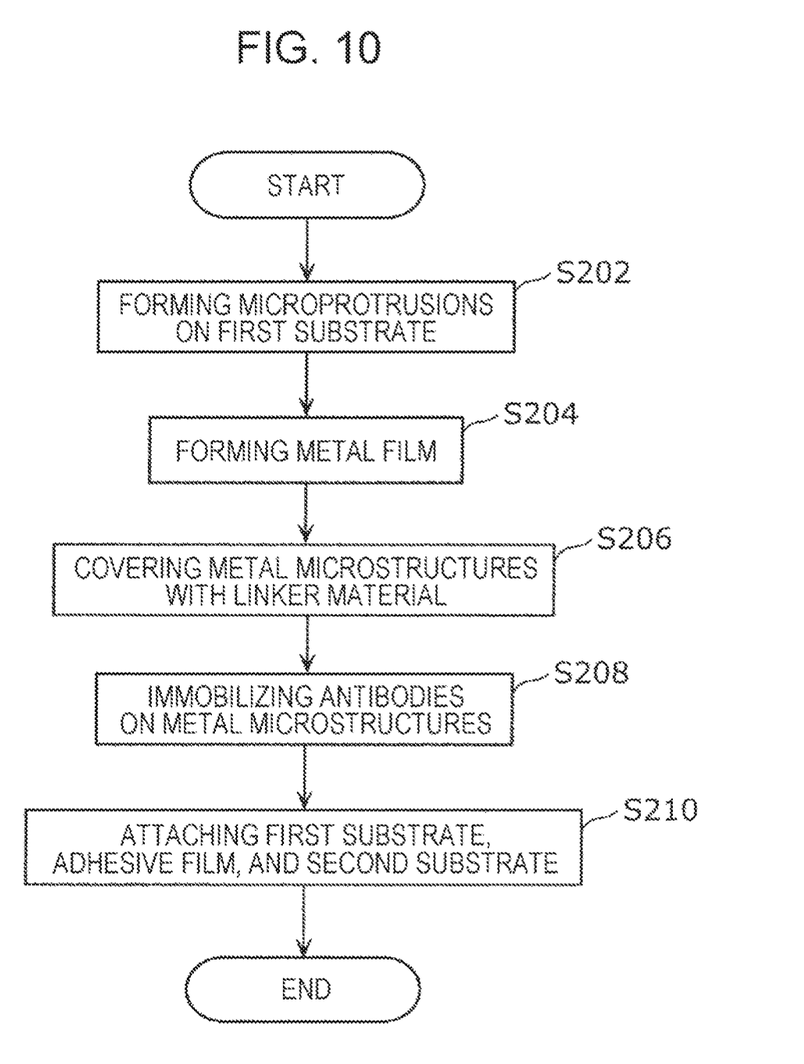
FIG. 10 is a flow chart indicating a method of producing the sensor substrate according to the embodiment.

Next, a method of producing the sensor substrate 10 is described with reference to FIG. 10. FIG. 10 is a flow chart indicating a method of producing the sensor substrate 10 according to the present embodiment.

First, multiple microprotrusions (including the first microprotrusions 111a and the second microprotrusions 111b) are formed on the first substrate 111 (S202). The method of forming the microprotrusions is not limited to a particular method. An example of the method includes a nanoimprint technology.

Next, the metal film 202 is formed on the first substrate 111 (S204). The metal film 202 is formed on the microprotrusions on the first substrate 111 to have discrete sections spaced apart from each other. For example, the metal film 202 may be patterned only on portions corresponding to the measuring portions 12 illustrated in FIG. 3.

Next, the metal microstructures 121 are covered by the linker material 203 (S206). For example, the first substrate 111 is soaked in a SAM solution to have a SAM film only on the metal film 202.

Next, an immobilized antibody is immobilized on the metal microstructure 121 (S208). For example, a VHH antibody is made to form a peptide bond with the SAM film. Since the area without the metal film 202 does not have the SAM film, the antibody is not immobilized on the area.

Finally, the first substrate 111 having the immobilized antibody that has been immobilized, the adhesive film 112, and the second substrate 113 are attached together (S210). The attachment may be carried out at a pressure lower than the atmospheric pressure. In particular, the pressure may be greater than or equal to 0.1 kPa and smaller than or equal to 10 kPa. This reduces the possibility that the sensor substrate 10 will have air bubbles therein.

The first substrate 111, the adhesive film 112, and the second substrate 113 may be attached together by being pressed on a ceramic stage having extremely high smoothness and stiffness by using a diaphragm. The diaphragm is a semi-flexible sheet fixed at the periphery and has a rounded shape. This reduces warping of the sensor substrate 10 and reduces the possibility that air bubbles will enter a space between the first substrate 111 and the adhesive film 112 and a space between the adhesive film 112 and the second substrate 113. The adhesive film 112 may have a thickness of greater than or equal to 50 μm and less than or equal to 200 μm. This reduces deformation of the sensor substrate 10 and achieves effective attachment of the first and second substrates 111 and 113.

Effects

As described above, in the sensor substrate 10 according to the present embodiment, the adhesive film 112 having the slits 122 is sandwiched between the first substrate 111 and the second substrate 113. Thus, the slits 122 in the adhesive film 112 can form flow passages, eliminating the need of forming flow passages in the first substrate 111. This enables high-sensitive detection while allowing the first substrate 111 to keep the transmitting properties.

Furthermore, the adhesive film eliminates the need of an adhesive that attaches the first substrate 111 to the second substrate 113. The adhesive film, which is less flowable than an adhesive, is unlikely to flow into the flow passages. Furthermore, the adhesive film does not need to be cured, reducing denaturalization of the immobilized antibody.

Furthermore, in the sensor substrate 10 according to the present embodiment, the second microprotrusions 111b not covered by the metal film 202 can be disposed around the first microprotrusions 111a covered by the metal film 202. This can reduce leakage of the sample through the flow passages in the measuring portions 12. The first microprotrusions 111a covered by the metal film 202 are hydrophilic due to the SAM film. Thus, the sample readily flows on the first microprotrusions 111a. However, the second microprotrusions 111b not covered by the metal film 202 are hydrophobic because the second microprotrusions 111b are not covered by the SAM film and the resin material is exposed. Thus, it is easy for the sample to flow in the flow passages in the measuring portions 12 and the sample is unlikely to leak to the hydrophobic area outside the flow passages. This can reduce liquid leakage (crosstalk) of the sample between the adjacent measuring portions.

Furthermore, fine gaps between the second microprotrusions 111b are available for removal of bubbles in the sample between the first microprotrusions 111a. This allows the sample to readily fill in the gaps between the first microprotrusions 111a, accelerating antigen-antibody reaction.

Example

Hereinafter, the present disclosure is described in more detail by using an example, but the present disclosure is not limited thereto.

In this example, a resin substrate having a nanostructure with multiple pillars (cylindrical microprotrusions) formed by a nanoimprint technology was used as the first substrate. The pillar has a height of 200 nm and a diameter of 230 nm. The pitch between the pillars is 460 nm. A metal film having a thickness of 400 nm was formed on the resin substrate by sputtering to produce metal microstructures. Excitation light having a wavelength of 785 nm was emitted from a light source to the metal microstructure, and fluorescence having a wavelength of 800 nm was produced by the fluorescent substance. In the metal microstructure, the absorption peak due to sharp plasmon resonance was found in a wavelength range of 650 nm to 850 nm.

The metal microstructure was soaked into the SAM solution overnight in an incubator of 40° C. to form a SAM film on the metal microstructure.

The SAM solution was produced according to the following procedure. First, Carboxy-EG6-undekanethiol and Hydroxy-EG3-undecanethiol were each diluted with ethanol to be 1 mM ($10^4$ mol/L) and were mixed. Then, the mixture was diluted fivefold with ethanol to produce the SAM solution.

Then, the carboxyl group at the end of the SAM film and the amino group at the end of the first VHH antibody were joined by a peptide bond through EDC/NHS reaction to immobilize the first VHH antibody on the SAM film.

The first substrate produced as above was attached to the second substrate with a two-sided adhesive film by using a vacuum bonder.

Figure 11:
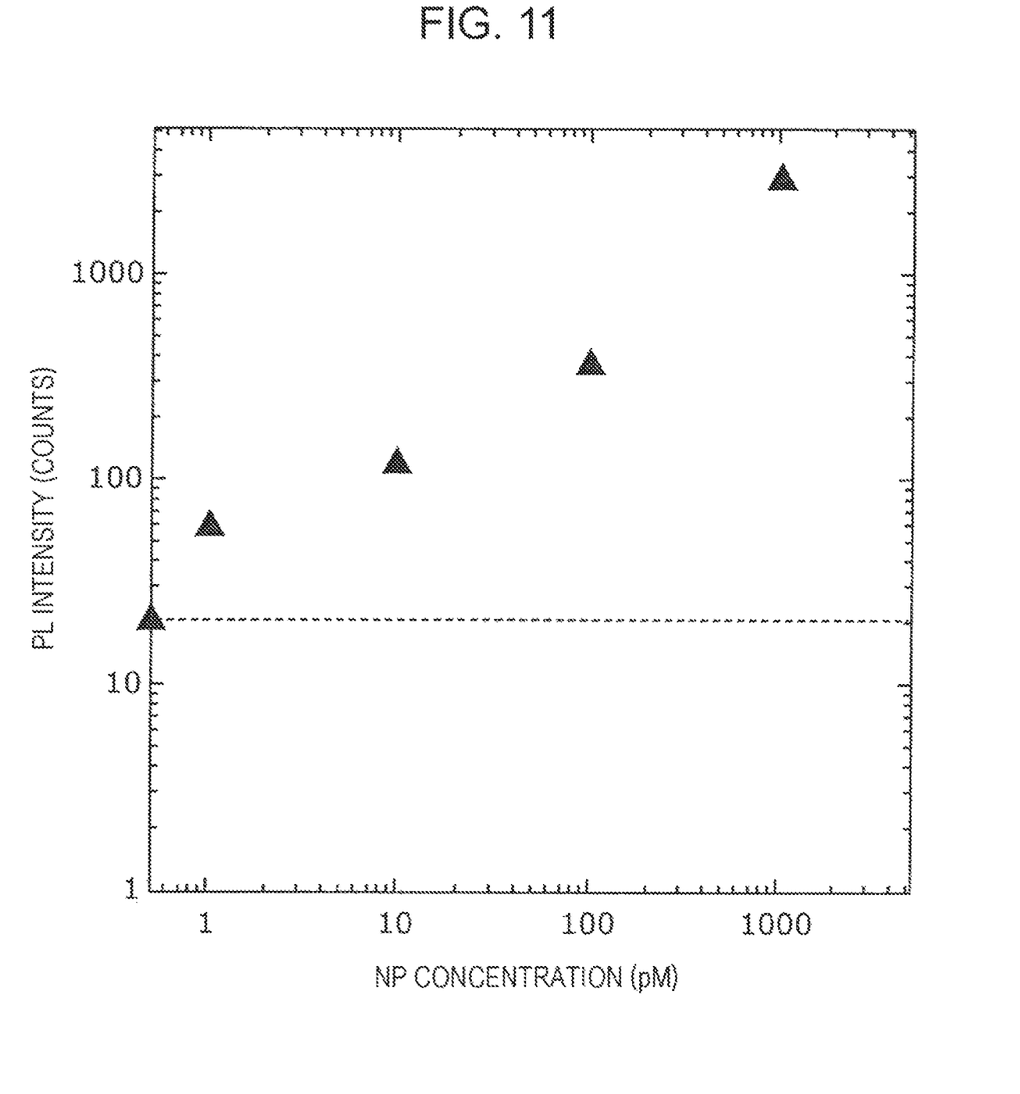
FIG. 11 is a graph indicating detection sensitivity of the sensor substrate according to an example.

A solution including an influenza virus nucleoprotein (NP), which is an analyte, and a second VHH antibody fluorescently labelled with an organic dye was sent from the supply hole to the discharge hole. FIG. 11 indicates data demonstrating detection sensitivities of the sensor substrate at various NP concentrations of 0, 1, 10, 100, and 1000 pM.

As indicated in FIG. 11, in this example, the NP concentration dependence was found in the PL intensity. Thus, the antigen-antibody reaction in the sensor substrate was confirmed. Further, the extremely low NP concentration of 1 pM was detected, verifying that the sensor substrate is able to perform highly sensitive detection. In the known technology, the minimum detectable concentration was 500 mM. The present technology has higher sensitivity than the known technology by $5\times10^{11}$. The sensitivity is high enough to detect the virus concentration in the air, which is extremely low.

OTHER EMBODIMENTS

The sensor substrate according to one or more aspects of the present disclosure was described above based on the embodiment, but the present disclosure should not be limited thereto. Various changes added to the embodiment by a person skilled in the art may be within the scope of one or more aspects of the present disclosure without departing from the spirit of the present disclosure.

For example, in the above-described embodiment, the sensor substrate is a circular plate, but the present disclosure is not limited to this. For example, the sensor substrate may be a polygonal plate (such as a rectangular plate) or an elliptical plate. In such a case, the measuring portions may be arranged in a matrix.

In the above-described embodiment, the sensor substrate has the multiple measuring portions, but the present disclosure is not limited to this. For example, the sensor substrate may have only one measuring portion.

In the above-described embodiment, the first substrate has the microprotrusions over the entire surface, but the first substrate may have only the first microprotrusions. In other words, the second microprotrusions around the first microprotrusions may be eliminated.

The sensor substrate according to the present disclosure is applicable to a detection system that determines a concentration of virus floating in the air in a room with high sensitivity to reduce the risk of virus infection to the people in the room.

What is claimed is:

1. A sensor substrate comprising:
a first substrate having first microprotrusions provided on the surface thereof and covered by a metal film;
an adhesive film disposed on the surface of the first substrate and having a slit; and
a second substrate that is transparent, disposed on the adhesive film, and having a first through hole and a second through hole,
wherein
each of the first through hole and the second through hole is in communication with the slit, and
the first microprotrusions overlap the slit in a plan view.

2. The sensor substrate according to claim 1, wherein
the first substrate further has second microprotrusions which has not been covered by the metal film, and
the second microprotrusions are located around the first microprotrusions.

3. The sensor substrate according to claim 1, wherein
the first microprotrusions are arranged at a regular interval.

4. The sensor substrate according to claim 3, wherein
the first microprotrusions are arranged in an equilateral triangular lattice.

5. The sensor substrate according to claim 4, wherein
each of the first microprotrusions has a cylindrical shape.

6. The sensor substrate according to claim 5, wherein
a pitch between adjacent two of the first microprotrusions is greater than or equal to 300 nm and less than or equal to 500 nm,
the cylindrical shape has a diameter of greater than or equal to 150 nm and less than or equal to 250 nm, and
the cylindrical shape has a height of greater than or equal to 100 nm and less than or equal to 300 nm.

7. The sensor substrate according to claim 1, wherein
the metal film is formed of any one of gold, silver, and an alloy containing gold or silver as a main component.

8. The sensor substrate according to claim 1, further comprising:
a first specific binding substance immobilized on the first microprotrusions covered by the metal film, wherein
the first specific binding substance is capable of being specifically bound to an analyte.

9. The sensor substrate according to claim 8, wherein
the first specific binding substance is a VHH antibody.

10. The sensor substrate according to claim 8, wherein
the metal film is covered by a linker material, and
the first specific binding substance has been immobilized on the first microprotrusions through a peptide bond with the linker material.

11. The sensor substrate according to claim 10, wherein
the linker material includes an alkyl chain with greater than or equal to 10 carbon atoms and a polyethylene glycol chain.

12. The sensor substrate according to claim 1, wherein
the adhesive film includes a silicone adhesive.

13. The sensor substrate according to claim 12, wherein
the adhesive film has a thickness of greater than or equal to 50 μm and less than or equal to 200 μm.

14. The sensor substrate according to claim 13, wherein the adhesive film has a three-layer structure including, in this order, a silicone adhesive layer, a polyimide layer, and a silicone adhesive layer.

15. The sensor substrate according to claim 1, wherein the second substrate is formed of polycarbonate.

16. A method of producing a sensor substrate, the method comprising:
forming first microprotrusions on a surface of a first substrate;
forming a metal film on the first microprotrusions; and
attaching the first substrate and a second substrate to each other with an adhesive film in such a manner that the adhesive film is located between the first substrate and the second substrate,
wherein
the adhesive film has a slit,
the second substrate has a first through hole and a second through hole,
each of the first through hole and the second through hole is in communication with the slit, and
the first microprotrusions overlap the slit in a plan view.

17. The method of producing a sensor substrate according to claim 16, wherein
the attaching is performed at a pressure lower than an atmospheric pressure.

18. The method of producing a sensor substrate according to claim 17, wherein
the attaching is performed at a pressure greater than or equal to 0.1 kPa and less than or equal to 10 kPa.

19. The method of producing a sensor substrate according to claim 16, wherein
the metal film is formed by sputtering.

* * * * *